United States Patent [19]

Young

[11] 4,294,668
[45] Oct. 13, 1981

[54] METHOD OF MEASURING OXYGEN AND PROCESS FOR PRETREATING A SOLID ELECTROLYTE OXYGEN GAS SENSING ELEMENT

[75] Inventor: Ching T. Young, Troy, Mich.

[73] Assignee: Bendix Autolite Corporation, Fostoria, Ohio

[21] Appl. No.: 158,843

[22] Filed: Jun. 12, 1980

Related U.S. Application Data

[62] Division of Ser. No. 942,102, Sep. 13, 1978, abandoned.

[51] Int. Cl.³ .......................................... G01N 27/58
[52] U.S. Cl. ............................... 204/1 T; 204/195 S
[58] Field of Search ............................. 204/195 S, 1 S

[56] References Cited

U.S. PATENT DOCUMENTS

| | | | |
|---|---|---|---|
| 3,514,377 | 5/1970 | Spacil et al. | 204/1 T |
| 3,691,023 | 9/1972 | Ruka et al. | 204/1 T |
| 3,699,032 | 10/1972 | Rapp | 204/195 S |
| 4,021,326 | 5/1977 | Pollner et al. | 204/195 S |
| 4,136,000 | 1/1979 | Davis et al. | 204/195 S |
| 4,158,166 | 6/1979 | Isenberg | 204/195 S X |
| 4,170,530 | 10/1979 | Watanabe et al. | 204/195 S |

OTHER PUBLICATIONS

J. E. Bauerle, J. Phys. Chem. Solids, vol. 30, pp. 2657–2670, (1969).
N. Pizzini et al., J. Appl. Electrochem., vol. 3, pp. 153–159, (1973).

Primary Examiner—G. L. Kaplan
Attorney, Agent, or Firm—William G. Kratz, Jr.; Raymond J. Eifler

[57] ABSTRACT

An activated solid electrolyte oxygen gas sensing element with increased voltage output, shortened switching time and reduced internal resistance, the sensing element having inner and outer conductive catalyst electrodes thereon, is produced by subjecting the outer surface with the outer electrode to a nonoxidizing atmosphere and applying a direct current to the element while the same is at an elevated temperature, the current being applied with the outer electrode as an anode.

13 Claims, No Drawings

METHOD OF MEASURING OXYGEN AND PROCESS FOR PRETREATING A SOLID ELECTROLYTE OXYGEN GAS SENSING ELEMENT

This is a division of application Ser. No. 942,102, filed Sept. 13, 1978 and now abandoned.

BACKGROUND OF THE INVENTION

The solid electrolyte-type oxygen sensor, in conjunction with a three-way catalyst converter, has been demonstrated to be an effective device for reduction of objectionable automotive emission by closed-loop control of the air-fuel mixture for the engine. The sensor comprises a sensor element which is generally formed as a stabilized zirconia solid electrolyte body in a thimble shape with both its inner and outer surfaces coated with a layer of a conductive catalyst electrode, such as a layer of platinum. When heated in the exhaust manifold with the outer electrode subjected to the exhaust gas and the inner electrode exposed to the ambient air, the sensor develops an electrochemical potential between the two electrodes which varies with the oxygen concentration in the exhaust gas stream. A large step change in the electrical potential occurs when the exhaust gas changes its composition from rich to lean or lean to rich passing through the point of stoichiometry. The voltage switching is used as a feedback signal to control the inlet air-fuel ratio within a narrow band around stoichiometry.

The sensor characteristics which are necessary or desirable for effective closed-loop control of inlet air-fuel mixture are high voltage outputs, fast voltage switching in response to exhaust gas variation, and low internal resistance. Typically, for an effective sensor operating at 350° C. electrolyte temperature, the desired voltage outputs are 600 to 1000 millivolts on rich and −200 to 200 millivolts on lean; the switching response (defined to be the transient time between 300 and 600 millivolts of sensor voltage when the exhaust condition is suddenly changed from rich to lean or lean to rich) less than 300 milliseconds; and the internal resistance less than 200 kiloohms. At 800° C., the desired voltage outputs are 700 to 900 millivolts on rich and 0 to 150 millivolts on lean; the switching response less than 100 milliseconds; and the internal resistance less than 100 ohms.

The present invention relates to a process for improving the sensor performance in terms of voltage output, switching response time and internal resistance. The process involves the current activation treatment of the sensors under controlled conditions with an external direct current applied to the sensor element with the outer electrode connected to the positive terminal of the electrical supply, or, in other words, with the outer electrode as an anode and the inner electrode as a cathode. The applied current appears to activate both the outer and the inner electrodes and the electrode-electrolyte interfaces, while at the same time polarizing the solid electrolyte.

The present process provides for a one time treatment of the solid electrolyte oxygen gas sensor element which provides improved properties to the sensor, namely a high positive voltage output, a fast switching response and a low interal resistance.

SUMMARY OF THE INVENTION

Solid electrolyte oxygen gas sensor elements are activated so as to provide improved properties, the element comprising a solid electrolyte body having an inner conductive catalyst electrode on the inner surface thereof and an outer conductive catalyst electrode on the outer surface thereof, by subjecting the outer surface of the element, with its outer conductive catalyst electrode coating, to a nonoxidizing atmosphere and heating the element to an elevated temperature in excess of 450° C. While at said elevated temperature and with the outer conductive catalyst electrode in contact with a nonoxidizing atmosphere, a direct current is applied to the sensor element, with the outer electrode as an anode, with the current density thereof being at least 5 milliamps per square centimeter of the outer conductive catalyst electrode planar surface.

DETAILED DESCRIPTION OF THE INVENTION

The gas sensor element which is the subject of the present invention is generally in the shape of a closed tubular member, thimble-like, and is formed of a solid electrolyte, such as zirconium dioxide containing various stabilizing materials such as calcium oxide or yttrium oxide. The general shape of the sensor element and the compositions usable in forming such elements are known, with such conventional design described in U.S. Pat. No. 3,978,006 and other published literature. The preferred composition is a solid electrolyte body formed from a mixture of zirconium dioxide and stabilizing materials, such as calcium oxide or yttrium oxide.

To both the inner and outer surfaces of the solid electrolyte oxygen gas sensor element there are applied conductive catalyst electrodes. Generally, the inner conductive catalyst electrode is applied to the inner surface such as by applying a platinum paste, which may contain a glass frit, with the paste preferably covering the interior surface of the closed terminal end of the sensor element and extending to the shoulder of the electrolyte body. The electrolyte body, with the applied paste, is then fired at a temperature of 600°–1000° C. or higher, as known in the art, to convert the platinum paste coating into an electrically conductive catalytic inner electrode. The outer conductive catalyst electrode is applied to the outer surface of the electrolyte body by known means, such as thermal vapor deposition. Because of the intended exposure of the outer electrode to high temperatures and gas velocities during operation of the sensors, the same may be provided with a porous protective outer layer such as a layer of porous $Al_2O_3$-$MgO$ spinel.

The conductive catalyst electrodes are preferably formed from a platinum family-metal catalyst such as platinum, palladium, rhodium or mixtures thereof, with platinum being the preferred catalyst material.

In the present process, the solid electrolyte sensor element is treated by application of a direct current charge thereto, in a particular manner and under particular conditions which improve the properties of the element relative to untreated sensor elements and sensor elements of the prior art. The direct current charge is applied to the sensor element while the outer surface thereof, having the outer conductive catalyst coating, is at an elevated temperature and is subjected to a nonoxidizing aqueous atmosphere.

The elevated temperature to which the outer surface of the sensor element must be heated is in excess of about 450° C., with a temperature in the range of 600°–900° C. preferred. The temperature may be higher than this range and may be as high as about 1100° C., with the upper temperature limit for a particular sensor element being dependent upon the effect of such high temperatures upon the electrolyte composition. Too high a temperature would also cause deterioration of the catalytic layer of the sensor element.

While the outer surface of the sensor element, with its outer conductive catalyst electrode, is at such an elevated temperature, that electrode is subjected to a non-oxidizing atmosphere. It has been found that while a reducing, a neutral or an inert atmosphere is useful in the present invention, an oxidizing atmosphere, such as air, does not provide the results desired. Examples of reducing gases which may be used are carbon monoxide, hydrogen, or rich exhaust gas mixtures, while neutral gases, such as nitrogen, inert gases, such as argon, are also useful to provide the gaseous atmosphere during treatment under the present process. A small amount of water vapor may be present but it is not necessary. The preferred atmosphere is a neutral atmosphere comprising nitrogen.

While the outer surface of the sensor element, with its outer conductive catalyst coating, is at the elevated temperature and subjected to a nonoxidizing atmosphere, a direct current is applied to the sensor element with the outer electrode as an anode and the inner electrode as a cathode. A direct current power supply is thus connected to the conductive catalyst electrodes, with the outer electrode connected to the positive terminal and the inner electrode connected to the negative terminal of the power source.

The current charge is such that a current density is provided which is greater than 5 milliamperes per square centimeter of the outer conductor catalyst electrode planar surface. The term "current density" as used herein is determined by dividing the current (in milliamperes) by the planar surface area of the outer conductive catalyst electrode ($cm^2$) on the outer surface of the solid electrolyte body. The term "planar surface of the outer electrode" is used to define the surface that would be present if the conductive catalyst electrode were a smooth coating without porosity.

The preferred range of current density used in the present process is between about 20 to 150 milliamperes per square centimeter of the outer conductive catalyst electrode surface. Current densities below 5 $ma/cm^2$ are not effective in the present process, while current densities of much higher value can be used, to a point where the sensor element cannot withstand the shock and may shatter. The preferred range, however, has been found to provide the desired properties to the sensor element without deleterious effects upon the catalytic electrode or the solid electrolyte body.

The direct current is applied to the sensor element at the required elevated temperature and while the outer electrode is in the presence of a nonoxidizing gas for a period of time which will vary dependent upon the temperature, current density and other conditions. A period of current application, as low as two seconds, has been found to be sufficient, while much longer times may be used. A preferred time of application of the current, with the preferred temperature range and current density, is about six seconds to ten minutes. Where the longer time periods of current application are used, the sensor element may require a recovery treatment, that is holding the sensor element at the elevated temperature for a period of time after the current is turned off.

The following examples further illustrate the present invention. In these examples, the testing of thimbles, as sensor elements, to determine their performance in terms of voltage output under rich and lean conditions, the switching response to gas variation and their internal resistance, was made by inserting the thimbles into protective housings with conductive leads connected to the inner and outer electrodes to form sensors. The tests were conducted at 350° C. and at 800° C. with the 800° C. testing effected first.

The sensor performance tests were conducted by inserting the sensors into a cylindrical metal tube and exposing them to oxidizing and reducing gaseous atmospheres within the tube through use of a gas burner adjustable to produce such atmospheres. Sensors placed in the desired positions in the tube were heated to testing temperature and the voltage output measured using a volt meter. The output was also connected to an oscilloscope to measure the speed of response of the sensor when the burner flame was changed from rich to lean and from lean to rich. A routine test consisted of setting the flame to rich condition, measuring the voltage output of the sensor, switching the flame suddenly to lean condition, triggering the oscilloscope sweep at the same time to record the rich to lean switch of the sensor, switching the flame suddenly back to rich condition, again triggering the oscilloscope to record the sensor output change, and finally adjusting the flame to a lean condition and measuring the sensor output voltage. The switching time is defined as the time period required for the output voltage, as recorded on the oscilloscope to sweep between 600 and 300 millivolts. When the sensor output voltage under rich gas condition is less than 600 millivolts, the switching response time is not determinable (n/d) according to the criteria used for this switching response measurement. Rich voltage output measurements were then made with different known values of shunting resistance across the sensor terminals. These measurements provided data for calculating the internal resistance of the sensors.

A series of gas sensor electrolyte body thimbles was prepared, for use in the following examples, from ball-milled zirconia, yttria and alumina in a ratio of 80%, 14% and 6% by weight respectively, by isostatically pressing the same in the desired thimble shape and firing at high temperature.

EXAMPLE I

Six of the series of electrolyte body thimbles (PA-2, PA-3, PA-8, PA-9, PA-14 and PA-15) had an inner electrode applied to the inner surface thereof by coating the inner surface with a platinum suspension containing a glass frit for bonding purposes. The thimbles, with their inner electrodes, were then heated in an oxidizing atmosphere to burn off the organic constituents of the suspension and bond the platinum to the zirconia surface. The external platinum catalyst electrode was next applied to the outer surface of the thimble by known vapor deposition. A porous ceramic coating was applied over the external catalyst layer for protection. The thimbles were then formed into sensors and tested as to voltage output, switching response and internal resistance, as hereinbefore described. The results of the tests are listed in Table I under the designation "No Treatment."

The thimbles were then subjected to a current activation by inserting the thimbles, as sensors in a protective housing and with conductive leads, into a manifold, with the outer surface of the sensor elements thereof having the outer conductive catalyst coating thereon exposed, while preheated during a ten-minute period to a temperature of 750° C., in a flow of 0.5% CO in nitrogen, (with 0.01 mg/cm$^3$ water vapor when indicated as "wet"), at a flow rate of 710 cm$^3$/min. The inner conductive catalyst electrode was in contact with air, and the temperature of the sensor was taken at the bottom of the inner region of the sensor element. The sensors were then subjected to a direct current, as indicated, for a ten-minute period, the direct current charge applied at a current density of 100 milliamperes/cm$^2$ of the outer electrode planar surface. The direct current was then stopped and the sensor elements allowed a recovery period of ten minutes at said temperature and with the outer electrodes in said gas flow.

These sensors were then again tested as to voltage output, switching response and internal resistance. The results of these tests are listed in Table I under the heading "After Current Activation."

of high voltage output in the rich gas condition, fast switching response and very low internal resistance. The properties are achieved whether or not water vapor is present in the nonoxidizing gas in contact with the outer electrode. It should be noted, however, that such current treatment where the outer electrode is connected to the negative terminal of the power source, acting as a cathode, does not provide the exceptional properties achieved following the present claimed process.

EXAMPLE II

Seven further electrolyte body thimbles of the series (PA-16, PA-17, PA-18, PA-19, PA-12, PA-13 and PA-20) had inner and outer catalytic electrodes applied thereto as such application was effected in Example I, and formed into sensors and tested as in Example I. The results of these tests are listed in Table II under the designation "No Treatment." These sensor elements were then current activated as in Example I, except that the gaseous atmosphere contacting the outer surface of the sensor elements was not carbon monoxide but rather that indicated in Table II for each sensor ("wet" gas contained about 0.01 mg/cm$^3$ of water vapor). All of these seven sensor elements were subjected to the direct

TABLE I

| | | 350° Testing | | | | 800° Testing | | | | |
|---|---|---|---|---|---|---|---|---|---|---|
| | | Voltage Output | | Switching Response | | Internal Resistance | Voltage Output | | Switching Response | | Internal Resistance |
| Sensor | Treatment | Rich (mv) | Lean (mv) | RL (ms) | LR (ms) | (kΩ) | Rich (mv) | Lean (mv) | RL (ms) | LR (ms) | (Ω) |
| PA-2 | No Treatment | 88 | −269 | n/d | n/d | 616 | 755 | 56 | 15 | 75 | 778 |
| PA-3 | No Treatment | 275 | −148 | n/d | n/d | 529 | 759 | 77 | 15 | 55 | 224 |
| PA-8 | No Treatment | 277 | −101 | n/d | n/d | 513 | 767 | 59 | 10 | 40 | 211 |
| PA-9 | No Treatment | 285 | −143 | n/d | n/d | 431 | 771 | 77 | 10 | 45 | 260 |
| PA-14 | No Treatment | 160 | −199 | n/d | n/d | 467 | 778 | 51 | 10 | 40 | 131 |
| PA-15 | No Treatment | 131 | −239 | n/d | n/d | 462 | 780 | 88 | 15 | 70 | 384 |
| | After Current Activation | | | | | | | | | | |
| PA-2 | Outer Electrode as Cathode wet CO | 225 | −228 | n/d | n/d | 645 | 776 | 57 | 30 | 50 | 230 |
| PA-3 | Outer Electrode as Cathode wet CO | 243 | −241 | n/d | n/d | 454 | 755 | 48 | 25 | 40 | 105 |
| PA-8 | Outer Electrode as Anode wet CO | 868 | −39 | 70 | 50 | 25 | 809 | 73 | 10 | 15 | 15 |
| PA-9 | Outer Electrode as Anode wet CO | 881 | −31 | 50 | 40 | 23 | 814 | 79 | 10 | 20 | 14 |
| PA-14 | Outer Electrode as Anode dry CO | 926 | 12 | 70 | 50 | 16 | 816 | 79 | 25 | 35 | 12 |
| PA-15 | Outer Electrode as Anode dry CO | 905 | −9 | 100 | 65 | 25 | 805 | 66 | 20 | 25 | 14 |

As illustrated in Table I, the current activation treatment of the present process, where the outer conductive catalyst electrode is subjected to a nonoxidizing atmosphere, and with the sensor elements subjected to a direct current charge with the outer electrode as an anode, results in exceptional and consistent properties current with the outer electrode as an anode. The sensors were again tested as to voltage output, switching response and internal resistance. The results of these tests are listed in Table II under the designation "After Current Activation."

TABLE II

| | | 350° Testing | | | | | 800° Testing | | | | |
|---|---|---|---|---|---|---|---|---|---|---|---|
| | | Voltage Output | | Switching Response | | Internal Resistance | Voltage Output | | Switching Response | | Internal Resistance |
| Sensor | Treatment | Rich (mv) | Lean (mv) | RL (ms) | LR (ms) | (kΩ) | Rich (mv) | Lean (mv) | RL (ms) | LR (ms) | (Ω) |
| PA-16 | No Treatment | 239 | −69 | n/d | n/d | 713 | 782 | 83 | 10 | 50 | 405 |
| PA-17 | No Treatment | 129 | −206 | n/d | n/d | 896 | 771 | 62 | 15 | 55 | 467 |

TABLE II-continued

|  |  | 350° Testing | | | | | 800° Testing | | | | |
|---|---|---|---|---|---|---|---|---|---|---|---|
|  |  | Voltage Output | | Switching Response | | Internal Resistance | Voltage Output | | Switching Response | | Internal Resistance |
| Sensor | Treatment | Rich (mv) | Lean (mv) | RL (ms) | LR (ms) | (kΩ) | Rich (mv) | Lean (mv) | RL (ms) | LR (ms) | (Ω) |
| PA-18 | No Treatment | 156 | −190 | n/d | n/d | 755 | 788 | 79 | 15 | 50 | 292 |
| PA-19 | No Treatment | 92 | −244 | n/d | n/d | 950 | 781 | 78 | 15 | 55 | 289 |
| PA-12 | No Treatment | 225 | −111 | n/d | n/d | 483 | 768 | 52 | 15 | 45 | 198 |
| PA-13 | No Treatment | 119 | −192 | n/d | n/d | 972 | 753 | 53 | 15 | 45 | 405 |
| PA-20 | No Treatment | 82 | −278 | n/d | n/d | 655 | 792 | 72 | 20 | 50 | 414 |
|  |  | After Current Activation | | | | | | | | | |
|  | Gaseous Atmosphere |  |  |  |  |  |  |  |  |  |  |
| PA-16 | Wet N₂ | 884 | −33 | 70 | 50 | 25 | 819 | 81 | 10 | 15 | 16 |
| PA-17 | Wet N₂ | 913 | −12 | 60 | 40 | 17 | 813 | 81 | 15 | 15 | 12 |
| PA-18 | Dry N₂ | 923 | 0 | 60 | 40 | 17 | 815 | 78 | 25 | 30 | 12 |
| PA-19 | Dry N₂ | 925 | 0 | 80 | 60 | 17 | 816 | 76 | 20 | 20 | 11 |
| PA-12 | Wet Air | 896 | 93 ↓ | 1,900 | 50 | 29 | 867 ↓ | 83 | 10 | 30 | 46 |
| PA-13 | Wet Air | 902 | 132 ↓ | 3,300 | 40 | 18 | 863 ↓ | 79 | 10 | 30 | 48 |
| PA-20 | Dry Air | 871 | 146 ↓ | 8,700 | 50 | 28 | 895 ↓ | 84 | 30 | 45 | 66 |

As indicated by the test results listed in Table II, the present process is not effective if an oxidizing gas, such as air, is present in contact with the outer conductive catalyst electrode during the current application. As shown, while increase in voltage output is obtainable, as is reduction in internal resistance, where oxidizing gases are present, the switching response time is high and unacceptable. The arrows shown in the table indicate that the values with which they are associated were not stable but continuing to decrease.

EXAMPLE III

Six additional electrolyte body thimbles of the series (AE 26-5, AE 26-8, AE 26-3, AE 26-4, AE 26-6 and AE 26-7) had an inner electrode applied to the inner surfaces thereof by coating the inner surfaces with a platinum metal suspension without any glass frit present in the suspension. The thimbles and inner electrodes were then heated in an oxidizing atmosphere for a period of time, during which the organic constituents in the suspension were burned off and the platinum bonded to the zirconia surfaces. The external catalyst layer (platinum) was next applied to the outer surface of the thimbles by known thermal vapor deposition. A porous ceramic coating was applied over the external catalyst layer for protection. These thimbles were then formed into sensors and tested, as hereinbefore described, to determine the voltage output, switching response and internal resistance. The results of the tests are listed in Table III under the designation "No Treatment."

These thimbles were then subjected to a current activation by inserting the thimbles, as sensors in a protective housing and with conductive leads, into a manifold, with the outer surfaces of the sensor elements thereof having the outer conductive catalyst coating thereon exposed, while preheated during a ten-minute period to a temperature of 750° C., to a flow of dry nitorgen (710 cm³/min.). The sensors were then subjected to a direct current, for a time period as indicated in Table III, with the outer electrodes as anodes, the direct current charge applied at a current density as indicated in Table III. The direct current was then stopped and the sensor elements allowed a recovery period of ten minutes at said temperature and with the outer electrodes in said nitrogen flow.

These sensor elements were then tested again. The results of the tests are listed in Table III under the designation "After Current Activation."

TABLE III

|  |  | 350° Testing | | | | | 800° Testing | | | | |
|---|---|---|---|---|---|---|---|---|---|---|---|
|  |  | Voltage Output | | Switching Response | | Internal Resistance | Voltage Output | | Switching Response | | Internal Resistance |
| Sensor | Treatment | Rich (mv) | Lean (mv) | RL (ms) | LR (ms) | (kΩ) | Rich (mv) | Lean (mv) | RL (ms) | LR (ms) | (Ω) |
| AE 26-5 | No Treatment | 848 | 252 | 8,500 | 120 | 89 | 806 | 73 | 40 | 50 | 43 |
| AE 26-8 | No Treatment | 721 | 248 | 2,000 | 220 | 346 | 791 | 76 | 25 | 55 | 85 |
| AE 26-3 | No Treatment | 623 | 65 | 590 | 560 | 274 | 793 | 91 | 25 | 30 | 72 |
| AE 26-4 | No Treatment | 907 | 180 | 4,100 | 100 | 50 | 801 | 89 | 30 | 45 | 47 |
| AE 26-6 | No Treatment | 472 | 86 | n/d | n/d | 549 | 780 | 75 | 25 | 55 | 67 |
| AE 26-7 | No Treatment | 600 | 81 | 650 | 700 | 391 | 772 | 67 | 25 | 55 | 59 |
|  |  | After Current Activation | | | | | | | | | |
|  | Current Density (ma/cm²) | Time of Applying Current (Min.) |  |  |  |  |  |  |  |  |  |
| AE 26-5 | 4 | 10 | 813 | 200 | 5,000 | 110 | 47 | 805 | 89 | 20 | 50 | 45 |
| AE 26-8 | 8 | 10 | 961 | 60 | 170 | 60 | 10 | 801 | 83 | 15 | 15 | 17 |
| AE 26-3 | 20 | 10 | 868 | 33 | 60 | 40 | 33 | 810 | 84 | 25 | 15 | 11 |
| AE 26-4 | 100 | 10 | 961 | 54 | 100 | 50 | 26 | 821 | 86 | 20 | 15 | 11 |
| AE 26-6 | 100 | 0.5 | 939 | 39 | 90 | 50 | 34 | 818 | 85 | 25 | 25 | 11 |
| AE 26-7 | 100 | 0.1 | 795 | 51 | 75 | 65 | 80 | 803 | 87 | 15 | 20 | 14 |

The test results of Table III illustrate the effect of the current density upon the present process, wherein current densities below about 5 ma/cm² of the planar surface of the outer conductive catalyst electrode do not give the desired results. Also, as illustrated, a time of application of the current as low as 0.1 minute (6 seconds) under the process conditions is effective, as shown by the improved properties of sensor element AE 26-7.

EXAMPLE IV

Four additional electrolyte body thimbles of the series (AP-17, AP-18, PA-4 and PA-11) had inner and outer catalytic electrodes applied thereto as such application was effected in Example I, and were formed into sensors and tested as in Example I. The results of these tests are listed in Table IV under the designation "No Treatment."

Two of the sensor elements, AP-17 and AP-18, were then subjected to a direct current, as in Example I, except that dry nitrogen was used in place of carbon monoxide, and the current application time was five minutes with the outer electrode as an anode, followed by five minutes with the outer electrode as a cathode (100 ma/cm²).

The other two sensor elements, PA-4 and PA-11, were subjected to the current activation steps of Example I, except that instead of using a direct current of the density indicated in Example I, the current applied was 60-cycle, 5 volt alternating current.

After these treatments, the sensors were again tested as to voltage output, switching response and internal resistance. The results of the tests are listed in Table IV under the designation "After Treatment."

It is evident from the test results of Table IV that the 60-cycle alternating current does not give the beneficial properties achieved by the direct current treatment of the present process, especially fast switching response. While some increase in voltage output and some lowering of internal resistance are effected, the results are not nearly as beneficial, note PA-4 and PA-11. In the process, however, an additional current treatment with the outer electrode as cathode, so long as a period of direct current activation with the outer electrode as anode is effected, does not give results as poor as those obtained when a 60-cycle alternating current is used.

EXAMPLE V

Three additional electrolyte body thimbles of the series (AP-11, AP-52 and AP-54) had inner and outer electrodes applied thereto following the procedure of Example I. The sensor elements were then tested for voltage output, switching response and internal resistance as in Example I; the results of these tests being listed in Table V under the designation "No Treatment." These thimbles were then subjected to a current activation step by inserting the thimbles, as sensors in a protective housing and with conductive leads, into a manifold with the outer surfaces of the sensor elements having the outer conductive catalyst coating thereon exposed to a flow of dry nitrogen gas (710 cm³/min.) The sensors were preheated to the temperature indicated in Table IV during a ten minute period and, at that temperature and with the flow of nitrogen gas continuing, a direct current was applied, with the outer electrodes as anodes for ten minutes at a current density of 100 ma/cm². A ten-minute recovery period followed after the current ceased, with the outer electrodes at the temperature indicated and in contact with the nitrogen.

These sensor elements were then again tested. The test results are listed in Table V under the heading "After Current Activation."

TABLE IV

| Sensor | Treatment | Gaseous Atmosphere | Current | 350° Testing ||||| 800° Testing |||||
|---|---|---|---|---|---|---|---|---|---|---|---|---|
| | | | | Voltage Output || Switching Response || Internal Resistance | Voltage Output || Switching Response || Internal Resistance |
| | | | | Rich (mv) | Lean (mv) | RL (ms) | LR (ms) | tance (kΩ) | Rich (mv) | Lean (mv) | RL (ms) | LR (ms) | tance (Ω) |
| AP-17 | No Treatment | | | 266 | −99 | n/d | n/d | 641 | 796 | 84 | 20 | 30 | 60 |
| AP-18 | No Treatment | | | 112 | −198 | n/d | n/d | 2,107 | 799 | 70 | 20 | 45 | 210 |
| PA-4 | No Treatment | | | 243 | −62 | n/d | n/d | 418 | 749 | 69 | 10 | 25 | 62 |
| PA-11 | No Treatment | | | 236 | −108 | n/d | n/d | 919 | 728 | 66 | 15 | 60 | 443 |
| After Treatment ||||||||||||||
| AP-17 | | Dry N² | * | 881 | −21 | 50 | 45 | 18 | 823 | 72 | 25 | 35 | 19 |
| AP-18 | | Dry N² | * | 884 | −25 | 45 | 50 | 19 | 812 | 75 | 25 | 25 | 11 |
| PA-4 | | Wet CO | Alt. current 5v | 728 | 12 | 570 | 230 | 108 | 806 | 81 | 20 | 20 | 34 |
| PA-11 | | Wet CO | Alt. current 5v | 553 | −103 | n/d | n/d | 190 | 801 | 59 | 15 | 20 | 81 |

*5 min. outer electrode as anode & 5 min. outer electrode as cathode

TABLE V

| Sensor | Treatment | 350° Testing ||||| 800° Testing |||||
|---|---|---|---|---|---|---|---|---|---|---|---|
| | | Voltage Output || Switching Response || Internal Resistance | Voltage Output || Switching Response || Internal Resistance |
| | | Rich (mv) | Lean (mv) | RL (ms) | LR (ms) | tance (kΩ) | Rich (mv) | Lean (mv) | RL (ms) | LR (ms) | tance (Ω) |
| AP-11 | No treatment | 81 | −206 | n/d | n/d | 1,739 | 808 | 85 | 25 | 45 | 375 |
| AP-52 | No Treatment | 372 | 13 | n/d | n/d | 805 | 758 | 60 | 20 | 50 | 80 |
| AP-54 | No Treatment | 128 | −256 | n/d | n/d | 1,751 | 741 | 72 | 20 | 70 | 328 |

TABLE V-continued

| | | 350° Testing | | | | | 800° Testing | | | | |
|---|---|---|---|---|---|---|---|---|---|---|---|
| | | Voltage Output | | Switching Response | | Internal Resistance | Voltage Output | | Switching Response | | Internal Resistance |
| Sensor | Treatment | Rich (mv) | Lean (mv) | RL (ms) | LR (ms) | (kΩ) | Rich (mv) | Lean (mv) | RL (ms) | LR (ms) | (Ω) |
| | | | | After Current Activation | | | | | | | |
| | Temp. °C. | | | | | | | | | | |
| AP-11 | 750 | 910 | −3 | 100 | 65 | 17 | 814 | 77 | 25 | 25 | 15 |
| AP-52 | 600 | 790 | −130 | 40 | 60 | 13 | 778 | 70 | 15 | 20 | 13 |
| AP-54 | 450 | 284 | −258 | n/d | n/d | 391 | 730 | 47 | 20 | 110 | 369 |

As is shown by the test results, the use of temperatures of about 450° C. and below do not give the desired improved properties, even where the other parameters of the present process are present, for sensor elements that have an inner catalytic coating containing a flux material. Where no flux material is present on the inner coating, temperatures in the range of 450° C. are acceptable but, in any event, a temperature in excess of 450° C. is required for proper processing.

EXAMPLE VI

A further six solid electrolyte thimbles of the series (AP-45, AP-46, AP-47, AP-48, AP-49 and AP-12) had inner and outer electrodes applied as in Example I. The sensor elements were then tested and the results of these tests are listed in Table VI under the designation "No Treatment." The sensor elements were then subjected to a current activation step as in Example V, except that the elevated temperature was 750° C. for each of the sensor elements while the time of current application and the time allowed for a recovery period were varied as indicated in Table VI. The sensor elements were then again tested, except that testing at 350° C. was effected first, followed by testing at 800° C. The results of the tests are listed in Table VI under the heading "After Curent Treatment."

nonoxidizing gas may be needed, the time of such recovery varying depending upon the other parameters of the current activation step. It should be noted that the internal resistance values of AP-47 and AP-49 at 350° C. are not includable since, due to the highly negative character of the output voltages, such values are not deemed representative.

There has been described a novel process for producing a solid electrolyte oxygen sensor element wherein the same is activated to given significantly improved properties.

What is claimed is:

1. A process for pretreating a solid electrolyte oxygen gas sensor element so as to increase the voltage output under rich gas conditions, shorten the switching response time, and reduce the internal resistance thereof, the sensor element comprising a solid electrolyte body having an inner conductive catalyst electrode on the inner surface, that is to be in contact with a reference gas during operation of the sensor, an outer conductive catalyst electrode coating on the outer surface thereof, that is to be in contact with a gas, the oxygen content of which is to be measured during operation of the sensor, and a porous protective coating over at least a portion of said outer electrode, comprising:

(a) heating the sensor element to an elevated tempera-

TABLE VI

| | | 350° Testing | | | | | 800° Testing | | | | |
|---|---|---|---|---|---|---|---|---|---|---|---|
| | | Voltage Output | | Switching Response | | Internal Resistance | Voltage Output | | Switching Response | | Internal Resistance |
| Sensor | Treatment | Rich (mv) | Lean (mv) | RL (ms) | LR (ms) | (kΩ) | Rich (mv) | Lean (mv) | RL (ms) | LR (ms) | (Ω) |
| AP-45 | No Treatment | 66 | −289 | n/d | n/d | 711 | 745 | 53 | 15 | 75 | 185 |
| AP-46 | No Treatment | 125 | −189 | n/d | n/d | 1,759 | 752 | 59 | 20 | 55 | 66 |
| AP-47 | No Treatment | 214 | −131 | n/d | n/d | 793 | 754 | 57 | 25 | 60 | 75 |
| AP-48 | No Treatment | 241 | −159 | n/d | n/d | 959 | 761 | 63 | 25 | 75 | 264 |
| AP-49 | No Treatment | 69 | −303 | n/d | n/d | 1,942 | 745 | 59 | 25 | 55 | 96 |
| AP-12 | No Treatment | 75 | −221 | n/d | n/d | 1,485 | 801 | 79 | 25 | 60 | 656 |
| | | | | After Current Activation | | | | | | | |
| | Time of Current (Min.) | | Time of Recovery (Min.) | | | | | | | | |
| AP-45 | 0.1 | 0 | 752 | −115 | 150 | 50 | 24 | 760 | 56 | 15 | 30 | 20 |
| AP-46 | 0.1 | 10 | 701 | −50 | 60 | 90 | 107 | 768 | 59 | 15 | 25 | 53 |
| AP-47 | 1 | 0 | −944 | −1876 | n/d | n/d | — | 785 | 81 | 15 | 15 | 22 |
| AP-48 | 1 | 10 | 870 | −45 | 200 | 60 | 20 | 791 | 62 | 20 | 40 | 30 |
| AP-49 | 10 | 0 | −1194 | −2110 | n/d | n/d | — | 767 | 60 | 15 | 25 | 12 |
| AP-12 | 10 | 10 | 898 | −8 | 120 | 80 | 8 | 810 | 75 | 15 | 20 | 18 |

As shown by the results in Table VI, where a short current application is used, less than one minute, the need for a recovery period may be obviated. Where a one minute or more application of the direct current is effected, however, a recovery period during which the sensor element is maintained at the elevated temperature and where the outer electrode is in contact with a ture in excess of 450° C. and subjecting the outer surface thereof, with said outer conductive catalyst coating, to a nonoxidizing atmosphere; and (b) applying a direct current to the sensor element, with said outer electrode as an anode, while said outer surface is at said elevated temperature and subjected to said nonoxidizing atmosphere, the current density thereof being at least 5 milliamperes per square centimeter of the planar surface of said outer conductive catalyst electrode.

2. The process for pretreating a solid electrolyte oxygen gas sensor element as defined in claim 1 wherein said sensor element is heated to a temperature in the range of 600°–900° C.

3. The process for pretreating a solid electrolyte oxygen gas sensor element as defined in claim 1 wherein said nonoxidizing gas is a reducing gas.

4. The process for pretreating a solid electrolyte oxygen gas sensor element as defined in claim 1 wherein said nonoxidizing gas is a neutral gas.

5. The process for pretreating a solid electrolyte oxygen gas sensor element as defined in claim 4 wherein said neutral gas comprises nitrogen.

6. The process for pretreating a solid electrolyte oxygen gas sensor element as defined in claim 1 wherein said current density is in the range of 20–150 milliamperes per square centimeter of the planar surface of said outer conductive catalyst electrode.

7. The process for pretreating a solid electrolyte oxygen gas sensor element as defined in claim 1 wherein, following the application of the direct current, the sensor element is maintained at said elevated temperature for a period of time after cessation of said current.

8. The process for pretreating a solid electrolyte oxygen gas sensor element as defined in claim 1 wherein said solid electrolyte body comprises zirconium dioxide.

9. The process for pretreating a solid electrolyte oxygen gas sensor element as defined in claim 8 wherein said inner and outer conductive catalyst electrodes are comprised of platinum.

10. The solid electrolyte oxygen gas sensor element pretreated according to the process of claim 1.

11. A process for pretreating a solid electrolyte oxygen gas sensor element so as to improve the operational properties thereof by increasing the voltage output under rich gas conditions, shortening the switching response time, and reducing the internal resistance thereof, wherein the sensor element comprises a zirconium dioxide solid electrolyte body having an inner conductive platinum electrode, that is to be in contact with a reference gas during operation of the sensor and an outer conductive platinum coating as an electrode over at least a portion of the outer surface thereof, that is to be in contact with a gas, the oxygen content of which is to be measured during operation of the sensor, and a porous protective coating over at least a portion of said outer electrode, comprising:
 (a) heating the sensor element to an elevated temperature in the range of 600°–900° C. and subjecting the outer surface thereof, with the platinum coating thereon, to a nitrogen atmosphere; and
 (b) applying a direct current to the sensor element, with said outer platinum coating electrode as an anode, while said outer surface is at said elevated temperature and in said nitrogen atmosphere, the current density thereof being about 20–150 milliamperes per square centimeter of the planar surface of said outer platinum coating electrode.

12. The process for pretreating a solid electrolyte oxygen gas sensor element as defined in claim 11 wherein, following the application of the direct current, the sensor element is maintained at said elevated temperature and with said outer platinum electrode in a nitrogen atmosphere for a period of time after cessation of said current.

13. A method for measuring the oxygen content of a gas with a solid electrolyte oxygen gas sensor element comprising a solid electrolyte body, an inner electrode on the inner surface, that is to be in contact with a reference gas during operation of the sensor, and an outer electrode on the outer surface, that is to be in contact with a gas, the oxygen content of which is to be measured during operation of the sensor, said method comprising:
 heating the sensor element to an elevated temperature in excess of 450 degrees C. and subjecting the outer surface thereof to a non-oxidizing atmosphere;
 applying a direct current to the sensor element, with said outer electrode as an anode, while said outer surface is at said elevated temperature and subjected to said non-oxidizing atmosphere, the current density thereof being at least 5 milliamperes per square centimeter of the planar surface of said outer electrode;
 removing the current from the sensor;
 exposing the outer electrode of said sensor to a gas the oxygen content of which is to be measured, with the inner electrode in contact with a reference gas; and
 measuring an electrical output from said sensor electrodes as a measure of the oxygen content of in said gas.

* * * * *